United States Patent [19]
Fini

[11] Patent Number: 5,858,015
[45] Date of Patent: Jan. 12, 1999

[54] CONTAINER FOR BLOOD

[75] Inventor: Massimo Fini, Mirandola, Italy

[73] Assignee: Dideco S.p.A., Italy

[21] Appl. No.: 802,011

[22] Filed: Feb. 18, 1997

Related U.S. Application Data

[63] Continuation of Ser. No. 314,149, Sep. 28, 1994, abandoned.

[30]    Foreign Application Priority Data

Sep. 29, 1993   [IT]   Italy ................................. TO93A0710

[51] Int. Cl.⁶ ........................... A61B 19/00; B01D 63/00
[52] U.S. Cl. .................................. 604/403; 128/DIG. 24; 210/321.6; 210/645; 422/44
[58] Field of Search ........................... 604/403, 408–410, 604/416; 128/DIG. 24; 210/321.6, 321.75, 321.84, 645; 422/44

[56]            References Cited

U.S. PATENT DOCUMENTS

| | | |
|---|---|---|
| 2,776,055 | 1/1957 | Adler . |
| 3,892,534 | 7/1975 | Leonard . |
| 4,229,290 | 10/1980 | Raj . |
| 4,276,170 | 6/1981 | Vaillancourt . |
| 4,294,594 | 10/1981 | Sloane, Jr. et al. ........................ 55/186 |
| 4,303,193 | 12/1981 | Latham, Jr. . |
| 4,341,538 | 7/1982 | Vadnay et al. . |
| 4,424,190 | 1/1984 | Mather, III et al. ..................... 604/403 |
| 4,466,888 | 8/1984 | Verkaart . |
| 4,484,936 | 11/1984 | Sakai . |
| 4,493,705 | 1/1985 | Gordon et al. . |
| 4,515,606 | 5/1985 | de Winter . |
| 4,525,182 | 6/1985 | Rising et al. . |
| 4,612,170 | 9/1986 | Luther et al. . |
| 4,643,713 | 2/1987 | Viitala . |
| 4,734,269 | 3/1988 | Clarke et al. . |
| 4,838,872 | 6/1989 | Sherlock . |
| 4,857,042 | 8/1989 | Schneider . |
| 4,959,062 | 9/1990 | Gellman .................................. 604/403 |
| 4,973,327 | 11/1990 | Goodrich, Jr. et al. . |
| 4,976,707 | 12/1990 | Bodicky et al. . |
| 5,049,146 | 9/1991 | Bringham et al. . |
| 5,211,913 | 5/1993 | Hagiwara et al. . |

FOREIGN PATENT DOCUMENTS 2077611   12/1981   United Kingdom .

Primary Examiner—Aaron J. Lewis
Assistant Examiner—Dennis Ruhl
Attorney, Agent, or Firm—Popovich & Wiles, P.A.

[57]            ABSTRACT

A container for blood having a generally rigid support which, in combination with a filter element such as a screen, defines a blood inlet chamber of substantially constant size and geometric shape. An expandable reservoir portion is associated with the support and, preferably, has a bellows-like configuration.

13 Claims, 2 Drawing Sheets

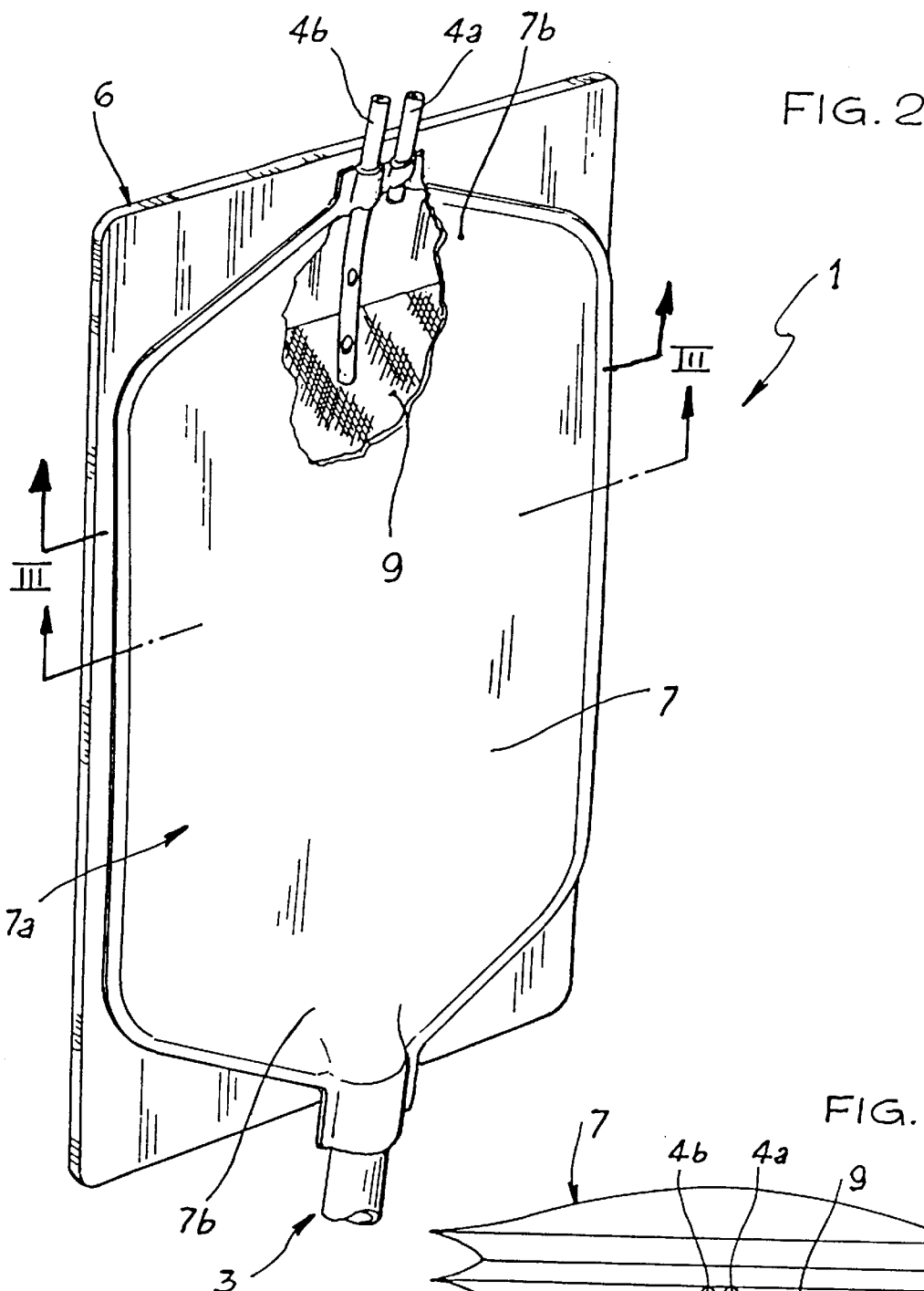

CONTAINER FOR BLOOD

This is a continuation of application Ser. No. 08/314,149 filed Sep. 28, 1994 now abandoned.

BACKGROUND OF THE INVENTION

The present invention relates to containers for blood. Containers of this type are currently used, for example, for transfusion purposes and in surgery for receiving and holding quantities of blood taken from the patient's body, for example, when the body is connected in an extracorporeal circulation system.

In general, two kinds of container of this type are known in the art: (1) those constituted by actual bags, envelopes of sheet material suitable for use in contact with blood (for example, PVC or polyurethane), forming generally flexible envelopes which can swell up to a greater or lesser extent according to the quantity of blood with them; and (2) hybrid solutions, such as that described in U.S. Pat. No. 4,424,190, in which the container comprises a concave, rigid, cylindrical shell and a flexible membrane. At rest, the membrane is disposed close to the internal wall of the shell and, when the blood flows into the container, the membrane bulges to a greater or lesser extent and, in the condition in which it is filled to the maximum permitted by the container, reaches a shape approximately complementary and symmetrical to that of the rigid shell.

Whichever solution is used, the container usually has at least one connection for the inlet of blood (taken from the patient's body), a vent for any air trapped in the blood, and at least one outlet. Particularly in applications in an operating environment (extracorporeal circulation systems with blood oxygenators) there is usually also a further connection for the return of blood from the cardiotomy, as well as a connection for recirculation from the oxygenator.

In this latter situation of use in particular, it is imperative to ensure that any air entrained by the blood flowing into the container is eliminated as completely as possible. In fact, any air trapped in the blood may fragment, even at a microscopic level, and this may result in more or less extensive damage to the patient to whom the blood is reinfused. For this reason, it is current practice for a container of the type specified above to have, downstream of the blood inlet connector, a filtering rete or screen (constituted, for example, by a sheet of polyester or polyamide with holes having diameters of the order of 40–200 microns) through which the blood entering the actual holding space of the container is intended to pass. The blood is filtered and the trapped air, which diffuises upwards to be discharged to the exterior through the corresponding vent, is consequently eliminated.

In both of the solutions considered above (a completely flexible bag and a container comprising a rigid shell), the filtering screen is usually also a flexible element which follows the deformable parts of the bag in their bulging and flattening movements resulting from the flow of blood into and out of the container. This solution is unsatisfactory from various points of view. In particular, it encourages the formation of preferred blood-flow directions within the container, resulting in the formation of stagnant regions. Thus, in many cases, as a result of its very flexibility, part of the filtering rete remains in a position close to the flexible wall of the container and adhering thereto when the container swells up, and the adhering portions of the screen thus perform no useful function.

SUMMARY OF THE INVENTION

The object of the present invention is to provide a container for blood which overcomes the problems recited above. According to the present invention, this object is achieved by virtue of a container having the specific characteristics recited in the following claims.

Briefly, in the solution according to the invention, instead of constituting a flexible element which is intended to move more or less freely within the container, possibly remaining close to the flexible walls of the container, a sheet filter is associated with a substantially rigid support which defines a blood inlet chamber of the container and keeps the filter evenly stretched out both in the rest condition and when the container is in use, without appreciable deformation resulting from the variations in the volume of the container itself. The entire surface area of the filtering screen is thus kept constantly exposed to the blood flow entering the bag.

Moreover, in the solution according to the invention, the flexible membrane (expandable) portion of the blood container can advantageously be produced in the form of a bellows. This enables a single type (or at least a small set) of structures to be used for supporting the filtering screen, in combination with a plurality of bellows of various sizes (and hence volumes) in order to form a selection of containers with different and graduated capacities (for example, 450, 650, and 950 cc) from a single base structure. This enables the user to select the container with the most suitable dimensions for the purpose envisaged at the time in question avoiding, for example, the need to select a large container for conditions of use in which the expected volume to be filled is small.

The invention will now be described, purely by way of non-limiting example, with reference to the appended drawings.

BRIEF DESCRIPTION OF THE DRAWINGS

FIG. 2 is a further perspective view of a container according to the invention, observed in the opposite direction from that of FIG. 1;

FIG. 4 is a sectional view corresponding approximately to the section of FIG. 3, showing an alternate embodiment of the invention; and FIG. 5 is a sectional view corresponding approximately to the section of FIG. 3, showing an alternate embodiment of the invention.

DETAILED DESCRIPTION OF THE PREFERRED EMBODIMENTS

Figure 1:
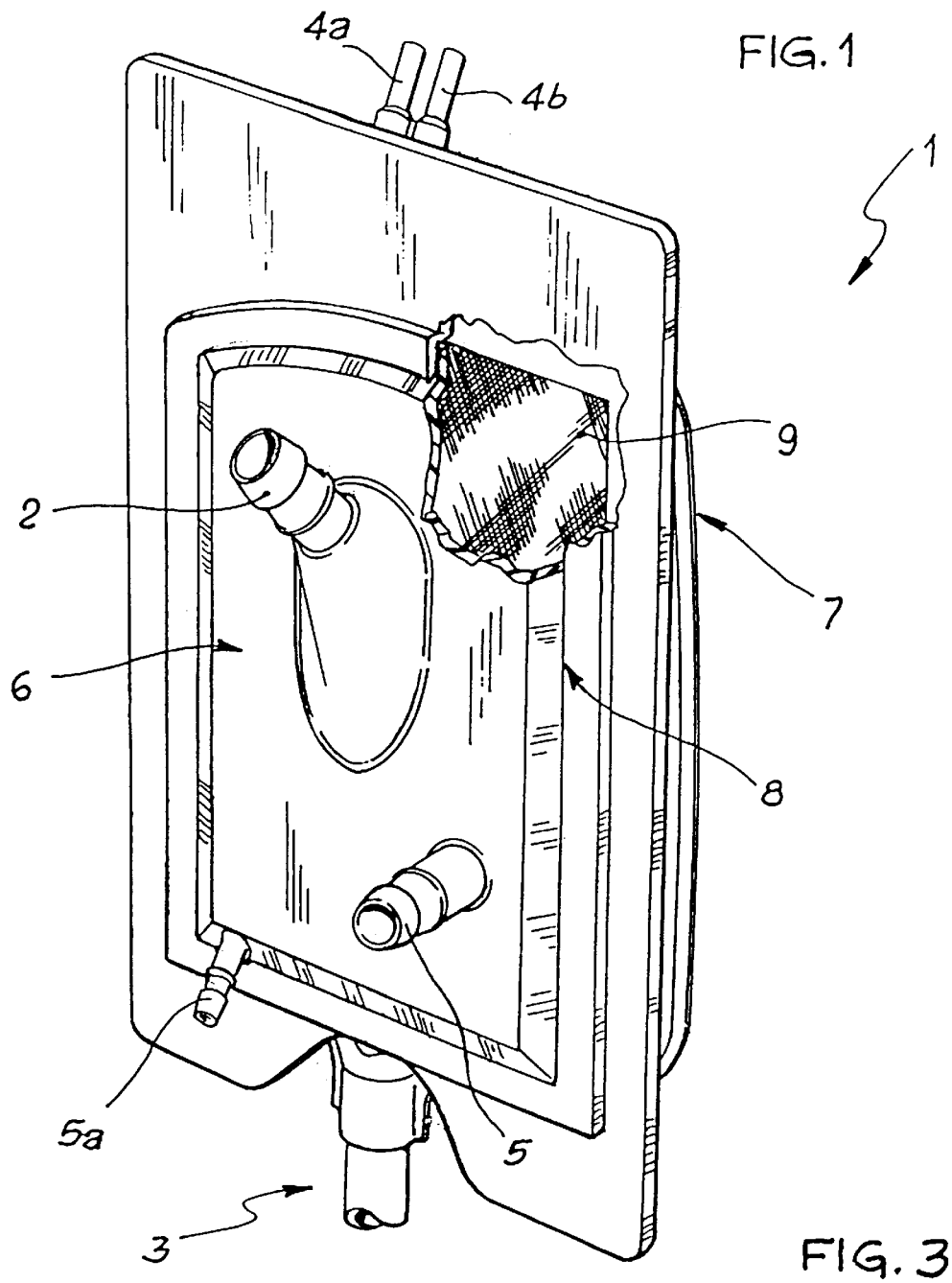
FIG. 1 is a general perspective view of a container for blood according to the invention.

As a premise, it should be noted that the term "blood" as used in all the parts of the present application (in particular, in the claims which follow) is intended to refer not only to actual blood but to all blood derivatives (plasma, etc.) in general and to biological liquids which may be dealt with by the container according to the invention.

In the appended drawings, a blood container (as defined above) is generally indicated 1. In particular, the embodiment shown relates to a blood container which can be used as a "venous bag" in an extracorporeal circulation system usable in a surgical-operating environment. In this use, the container 1 is intended to constitute a reservoir for holding the blood which has been taken from the patient's body and is intended subsequently to be readmitted to the patient's body after oxygenation treatment carried out in an oxygenator (not shown). For this purpose, the container comprises an inlet connector 2 through which the blood taken from the patient's body (by known means not shown) is admitted to the container 1, as well as an outlet connector 3 (situated in the portion of the container 1 which is in the lowest position under normal conditions of use) through which the blood flowing out of the container 1 is sent back to the patient's body (also by known means).

Two further connectors, indicated 4a and 4b, usually in the form of flexible tubes, are situated in the portion of the container 1 which is in the upper position in the normal condition of use. The connectors 4a and 4b are intended to form a route for the venting of any gas (typically air) which is trapped in the blood admitted to the container 1 and which is liberated from the blood as a result of the filtering effect achieved according to the criteria described further below.

In particular, the connector 4a is usually constituted by a flexible tube which opens in the top portion of the container 1 and the connector 4b forms a pipe which is also flexible and which usually extends within the container 1 for a certain distance so as to define a respective vent opening situated at a different, lower level than the vent opening defined by the connector 4a.

Also, connector 5 can be used to carry out (in known manner) the function of the so-called cardiotomy return. Finally, connector 5a (usually of smaller cross-section) can be used for the function of recirculating blood from the oxygenator. In general, the connectors described above are arranged for the connection of flexible tubes. This is in accordance with criteria which are widely known to those of skill in the art.

The container 1 is composed essentially of two parts: (1) a rigid support 6 on which the connectors 2, 5 and 5a are preferably fitted; and (2) a flexible portion or membrane 7 on which connectors 3, 4a, and 4b are preferably fitted, and which is constituted essentially by a bellows-like membrane structure which is fitted sealingly to the mouth portion of the support 6 so that, together with the support 6, it forms a closed, selectively expandable space.

Naturally, the term "rigid" used as a feature of the support 6 in the present description and, where appropriate, in the following claims, refers to the conditions (particularly the mechanical, hydrostatic, and hydrodynamic stresses) to which the support is subject in normal use under the action of a blood flow which is supplied to and discharged from the container, and in the normal situation of use. The support 6 is, therefore, defined as rigid since it can withstand the stresses to which it is subject in use without appreciable deformation. This contrasts with the feature "flexible" relating to membrane 7. In particular, reference is made to a "generally rigid" support 6 to take account of the fact that, at least in principle, the support 6 may be made pliable or flexible locally. What is important for the purposes of the implementation of the invention, however, is its general behavior.

As regards the selection of materials both for the support 6 and for the bellows-like portion 7, materials which have the following characteristics are generally used: haemocompatibility, at least in all the parts which are intended to come into contact with the blood (and hence at least on the internal faces both of the support 6 and of the bellows-like portion 7); a general rigidity (in the terms defined above) for the portion which is intended to form the support 6; and preferably, compatibility for connection by bonding (by the application of adhesive, heat-sealing, or by radio frequency welding, for example) so that the periphery of the bellows-like membrane 7 (see in particular the sectional views of FIGS. 3 to 5) can be welded along the periphery (the mouth portion) of the support 6. A selection of materials which has been found particularly satisfactory in this connection provides for the use of rigid PVC or polymethyl methacrylate (PMMA) for the support 6 and PVC for the bellows-like portion 7.

As can be seen from the drawings, in a preferred embodiment, the support 6 is of a generally flattened or planar shape and has a recessed, generally tank-shaped, portion 8, usually in its central region and extending over a significant portion of its area. By way of practical example, the support 6 shown in the appended drawings, may be compared to a kind of approximately rectangular tray. The means for blood inlet 2 is preferably located in the base wall 8a of the tank-shaped portion 8.

The mouth portion of the tank-shaped portion 8 of the support 6 bears (for example, as a result of welding or bonding) a sheet filter 9 which divides the space within the container 1 into two chambers: (1) a first chamber which acts as a blood inlet chamber into which the inlet connector 2, the cardiotomy return connector 5, and the recirculation connector 5a open (that is, the connectors which admit blood to the container 1), and which is defined by the tank-shaped portion 8 and by the filtering screen 9 extended over its mouth portion; and (2) a second, reservoir chamber defined by the bellows-like portion 7 and by the filtering screen 9. The outlet connector 3 and the vents 4a and 4b open into this second chamber precisely on account of their end mounting positions.

The first chamber has generally fixed dimensions since it is defined by a rigid body (in the terms defined above), that is, by the recessed, tank-like portion 8 of the support 6 and by an element (the filtering screen 9) which is kept anchored along its periphery to the periphery of the recessed portion 8. The geometrical shape of the blood inlet chamber thus remains almost unchanged both at rest when there is no blood in the container, and in operating conditions when blood is flowing into container 1 through connector 2. The second chamber, which is defined essentially by the flexible bellow-like portion 7, can vary its volume in dependence on the quantity of blood flowing into container 1.

Figure 3:
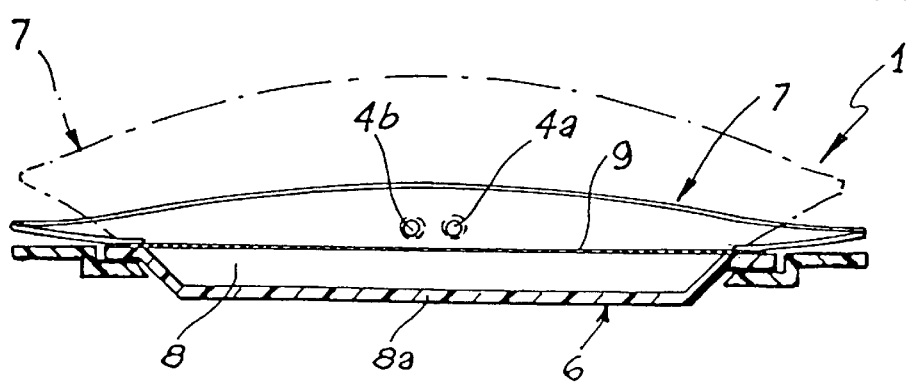
FIG. 3 is a sectional view taken on the line III—III of FIG. 2.

The sectioned view of FIG. 3 shows schematically two possible configurations adopted by the bellows-like portion 7. In particular, a configuration adopted by the flexible portion 7 in rest conditions, or in conditions in which the container 1 is only slightly filled, is indicated in continuous outline. The configuration which the bellows-like portion 7 can adopt when there is a certain amount of blood in the container 1, however, is shown in broken outline. It will be appreciated that the maximum volume of the deformation of flexible membrane portion 7 in practice defines the maximum volume to which the container 1 can be filled with blood. The quantity of blood housed in the inlet chamber defined by the tank-like portion 8 of the support 6 is in fact quite small.

A support 6 of the same type (this term meaning a type of support 6 having certain dimensional characteristics) can be associated with bellows-like portions 7 of various types, that is bellows-like portions having, for example, different numbers of pleats. Thus, if a container 1 with a small capacity is required, a bellows having a small number of pleats (even only one pleat, as in the embodiment shown in FIGS. 1 to 3, or one-half a pleat) will be coupled to the support 6. If a container of greater capacity is required, a bellows-like portion 7 with a larger number of pleats, for example, one and a half or two pleats, may be used as in the variants shown in FIGS. 4 and 5. Naturally for considerable ranges of capacity variations, the use of supports 6 of different dimensions could also be considered.

The sheet filter 9 is preferably fixed to the support 6 along a good portion of its periphery (for example, on three sides of the periphery of the mouth of the tank-shaped portion 8) so as to render it essentially undeformable, but nevertheless leaving a portion (which is intended to face upwards in use) which is free from the support to allow the rapid and unimpeded venting of air bubbles in the blood flowing into the container 1. In the embodiment shown (in which the mouth region of the tank-shaped portion 8 and the screen 9 are generally rectangular) this result can easily be achieved by avoiding the welding or bonding the side of the screen 9 which is intended to face upwards in use to the support 6 along, for example, one slightly arcuate and convex edge of the wall of the tank-shaped portion 8 (see FIG. 1).

It should also be stated that the embodiments shown in the appended drawings, in which the support 6 has an overall size corresponding approximately to the size of the bellows-like portion 7, should be considered purely exemplary. The embodiments have the advantage that the support 6 can be used to support the flexible membrane 7 of the container not only in the region of the sealed connection (the mouth of the tank-shaped portion 8a) but also in peripheral portions. Thus, when the container 1 is disposed in a vertical position or is inclined to the vertical, the support 6 further supports the flexible portion 7, preventing it from being subject to excessive bulging under the action of the blood contained therein.

The support 6 (and in particular its tank-shaped portion 8 which supports the filtering screen 9) may, however, be formed in a manner such that it has smaller dimensions than the area of the flexible portion 7 associated therewith. The invention may therefore also be applied, for example, to conventional flexible bags (by way of example, bags constituted by envelopes comprising two flexible sheets sealed together along their peripheries) in the form of a type of insert applied to one of the walls of the bag in order to define an inlet chamber for the blood (a debubbling chamber) of generally constant volume.

The foregoing also draws attention to the fact that although the bellows-like configuration shown for membrane 7 is preferred, it does not constitute an absolute necessity for the purposes of the implementation of the invention. For example, it is possible, whilst retaining a general configuration of the type shown in the drawings (that is, with a support 6 having an area approximately corresponding to that of the flexible portion of the container), to form the variable-volume portion of the container without the use of a bellows-like element, but simply by welding a sheet of generally flexible and resilient material along the periphery of the support 6. In this case, rather than leading to the unfolding of the flexible portion (as is the case of the bellows-like portion shown in the appended drawings), the filling of the container with blood brings about a certain bulging of the flexible (and resilient) sheet-like portion fitted on the rigid support 6. In order to prevent the reaction force of the membrane resulting in a net effect of pumping the blood towards the exterior of the container, the last solution mentioned is usually reserved for large containers (that is, containers in which the deformation force exerted on the resilient membrane is smaller for a given volume of blood contained).

As far as the support 6 is concerned, a generally curved shape, for example, an arcuate shape, may be used in order to bring the connectors 3, 4a and 4b to the extremities of the arcs.

In any case, whatever its structural details, the solution according to the invention has the basic advantage that the blood which flows into the container 1 (usually from the patient's body) collects in an inlet chamber of constant volume and geometrical shape, and then goes into the variable-volume reservoir chamber of the container after passing through the filtering screen 9.

It will be noted that, in the embodiment shown, the support 6 has a generally rectangular shape, whereas the bellows-like portion 7 (seen in plan and hence from an observation point which best identifies the shape of the peripheral connection to the rigid support 6) is of a generally hexagonal shape with a generally rectangular central portion 7a (FIG. 2) and two triangular end portions, indicated 7b, the sides of which converge in the apex regions in which the connectors 3, 4a and 4b are disposed. This converging configuration of the portions 7b is intended (in the case of the outlet connector 3) to direct the blood towards the outlet aperture of the container 1 like a funnel and (in the case of the vent connectors) to direct any aeriformns liberated from the blood towards the vents 4a, 4b like a chimney or hood. This prevents the local relaxation of flexible membrane 7 in the only slightly full condition from blocking the connectors.

Naturally, the principle of the invention remaining the same, the details of construction and forms of embodiment may be varied widely with respect to those described and illustrated, without thereby departing from the scope of the present invention.

I claim:

1. A blood reservoir, comprising:

(a) a rigid support having a recessed portion;

(b) a sheet filter for filtering blood, the sheet filter having a periphery which is fixedly attached to the rigid support and overlying the portion of the rigid support which is recessed, said sheet filter in a generally fixed position, the sheet filter and the overlied portion of the rigid support defining a blood inlet chamber having a substantially constant volume;

(c) a flexible membrane overlying the sheet filter and secured by a liquid-tight seal to the rigid support, defining a variable-volume reservoir chamber, the membrane being expandable upon the introduction of blood into the reservoir chamber to expand the reservoir chamber from a first, at rest, substantially empty position, to a second, expanded, substantially full position, the blood inlet chamber and reservoir chamber in fluid communication through the sheet filter;

(d) a cardiotomy return connector in fluid communication with the inlet chamber;

(e) a blood inlet in fluid communication with the inlet chamber; and (f) a blood outlet in fluid communication with the reservoir chamber.

2. The blood reservoir of claim 1, wherein the flexible membrane is secured to the rigid support at the periphery of the sheet filter.

3. The blood reservoir of claim 1, wherein the flexible membrane is secured to the rigid support outside of the periphery of the sheet filter.

4. The blood reservoir of claim 1, wherein the sheet filter is generally rectangular and is fixedly attached to the rigid support on three sides of the sheet filter.

5. The blood reservoir of claim 1, further comprising a vent in fluid communication with the reservoir chamber.

6. A blood reservoir, comprising:

(a) a rigid support having a recessed portion;

(b) a sheet filter for filtering blood, the sheet filter having a periphery which is fixedly attached to the rigid support and overlying the portion of the rigid support which is recessed, said sheet filter in a generally fixed position, the sheet filter and the overlied portion of the rigid support defining a blood inlet chamber having a substantially constant volume;

(c) a flexible membrane overlying the sheet filter and secured by a liquid-tight seal to the rigid support, defining a variable-volume reservoir chamber, the membrane being expandable upon the introduction of blood into the reservoir chamber to expand the reservoir chamber from a first, at rest, substantially empty position, to a second, expanded, substantially fill position, the blood inlet chamber and reservoir chamber in fluid communication through the sheet filter;

(d) a vent in fluid communication with the reservoir chamber, having a first and second vent pipe extending into the reservoir chamber, the second vent pipe extending into the reservoir chamber a distance further than the first vent pipe;

(e) a blood inlet in fluid communication-with the inlet chamber; and (f) a blood outlet in fluid communication with the reservoir chamber.

7. The blood reservoir of claim 1, wherein the rigid support has an arcuate shape.

8. The blood reservoir of claim 1, wherein the rigid support is made of PVC or polymethyl methacrylate.

9. The blood reservoir of claim 1, wherein the flexible membrane is made of PVC or polyurethane.

10. A blood reservoir, comprising:

(a) a rigid support having a recessed portion;

(b) a sheet filter for filtering blood, the sheet filter having a periphery which is fixedly attached to the rigid support and overlying the portion of the rigid support which is recessed, said sheet filter in a generally fixed position, the sheet filter and the overlied portion of the rigid support defining a blood inlet chamber having a substantially constant volume;

(c) a flexible membrane overlying the sheet filter and secured by a liquid-tight seal to the rigid support, the flexible membrane having a bellows configuration and defining a variable-volume reservoir chamber, the membrane being expandable upon the introduction of blood into the reservoir chamber to expand the reservoir chamber from a first, at rest, substantially empty position, to a second, expanded, substantially full position, the blood inlet chamber and reservoir chamber in fluid communication through the sheet filter;

(d) a blood inlet in fluid communication with the inlet chamber; and (e) a blood outlet in fluid communication with the reservoir chamber.

11. The blood reservoir of claim 1, wherein the flexible membrane is a generally planar, resilient sheet.

12. The blood reservoir of claim 1, wherein the flexible membrane has a hexagonal shape.

13. The blood reservoir of claim 1, wherein the rigid support extends outward from the periphery of the sheet filter and is planar.

* * * * *

UNITED STATES PATENT AND TRADEMARK OFFICE
CERTIFICATE OF CORRECTION

PATENT NO. : 5,858,015
DATED : January 12, 1999
INVENTOR(S) : Massimo Fini

It is certified that error appears in the above-identified patent and that said Letters Patent is hereby corrected as shown below:

Claim 6, line 17, replace "fill" with--full--;line 25, delete "-" between "Communication" and "with".

Signed and Sealed this

Twenty-seventh Day of June, 2000

Attest:

Q. TODD DICKINSON

*Attesting Officer*        *Director of Patents and Trademarks*